(12) United States Patent
Schreiber

(10) Patent No.: US 11,389,218 B2
(45) Date of Patent: Jul. 19, 2022

(54) POSITIONING DEVICE FOR FIXING A POLYAXIAL PLATE TO A TUBULAR BONE USING A HOLE SECTION

(71) Applicant: OT Medizintechnik GmbH, Munich (DE)

(72) Inventor: Ulrich Schreiber, Munich (DE)

(73) Assignee: OT MEDIZINTECHNIK GMBH, Munich (DE)

(*) Notice: Subject to any disclaimer, the term of this patent is extended or adjusted under 35 U.S.C. 154(b) by 29 days.

(21) Appl. No.: 16/646,996

(22) PCT Filed: Sep. 12, 2018

(86) PCT No.: PCT/EP2018/074617
§ 371 (c)(1),
(2) Date: Mar. 12, 2020

(87) PCT Pub. No.: WO2019/053065
PCT Pub. Date: Mar. 21, 2019

(65) Prior Publication Data
US 2020/0261129 A1    Aug. 20, 2020

(30) Foreign Application Priority Data
Sep. 13, 2017 (DE) .................... 10 2017 121 242.6

(51) Int. Cl.
*A61B 17/80* (2006.01)
*A61B 17/17* (2006.01)
*A61B 17/84* (2006.01)

(52) U.S. Cl.
CPC ........ *A61B 17/808* (2013.01); *A61B 17/1728* (2013.01); *A61B 17/8052* (2013.01); *A61B 17/848* (2013.01)

(58) Field of Classification Search
CPC .......................... A61B 17/808; A61B 17/1728
See application file for complete search history.

(56) References Cited

U.S. PATENT DOCUMENTS 7,727,236 B2 * 6/2010 Choe .................. A61B 17/1633
606/86 R
8,142,432 B2 * 3/2012 Matityahu .............. A61B 17/66
606/54
(Continued)

FOREIGN PATENT DOCUMENTS

DE        20013900 U1    6/2001
DE    102006016213 A1   10/2007
(Continued)

OTHER PUBLICATIONS

Translation of International Search Report for PCT/EP2018/074617 dated Mar. 21, 2019.
Search Report for DE 10 2017 121 242.6.

*Primary Examiner* — Anu Ramana
(74) *Attorney, Agent, or Firm* — Aird & McBurney LP

(57) ABSTRACT

The present invention relates to a positioning device comprising a plate holder with a first fastening device for releasably fastening the plate holder to the plate, and with a second fastening device; a receptacle for an adjustment device, wherein the adjustment device comprises at least one navigation device, and wherein the navigation device is designed to receive, at least in sections, an interlocking device, and/or an instrument for acting on the interlocking device and/or; wherein the receptacle comprises at least one third fastening device or is connected thereto; wherein one element from the group consisting of the second fastening device and the third fastening device comprises a hole section with a plurality of holes, and wherein the other element of the group is designed as an insertion section, wherein the insertion section and the holes are designed for releasably connecting the second fastening device to the third fastening device.

20 Claims, 8 Drawing Sheets

(56) References Cited

U.S. PATENT DOCUMENTS

| | | | | |
|---|---|---|---|---|
| 8,282,638 | B2* | 10/2012 | Choe | A61B 17/1633 606/80 |
| 8,328,809 | B2* | 12/2012 | Wenk | A61B 17/1728 606/71 |
| 9,155,575 | B2* | 10/2015 | Wenk | A61B 17/80 |
| 2005/0049594 | A1 | 3/2005 | Wack et al. | |
| 2007/0173836 | A1 | 7/2007 | Prien | |
| 2007/0276401 | A1* | 11/2007 | Choe | A61B 17/1728 606/96 |
| 2008/0132900 | A1 | 6/2008 | Prien et al. | |
| 2008/0188852 | A1 | 8/2008 | Matityahu | |
| 2009/0024132 | A1 | 1/2009 | Blain et al. | |
| 2011/0270319 | A1 | 11/2011 | Sheffer | |
| 2013/0012945 | A1* | 1/2013 | Chreene | A61B 17/1728 606/80 |
| 2015/0223824 | A1 | 8/2015 | Meberak | |
| 2016/0045238 | A1 | 2/2016 | Bohay et al. | |

FOREIGN PATENT DOCUMENTS

| | | |
|---|---|---|
| DE | 102014109935 A1 | 1/2016 |
| DE | 102016103681 A1 | 9/2017 |
| EP | 2745786 A2 | 6/2014 |
| ES | 2523021 T3 | 11/2014 |
| WO | 2016008849 A1 | 1/2016 |

\* cited by examiner

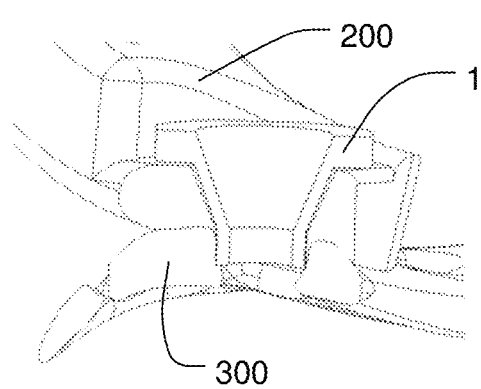
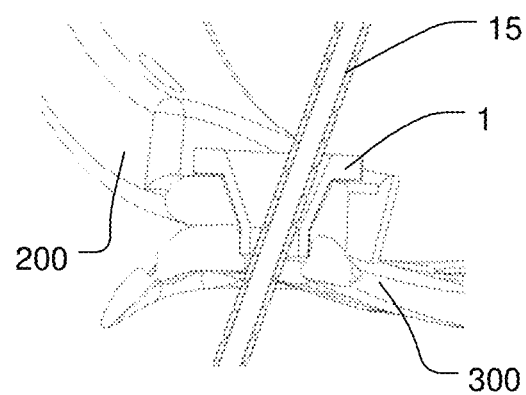
Fig. 9a  Fig. 9b
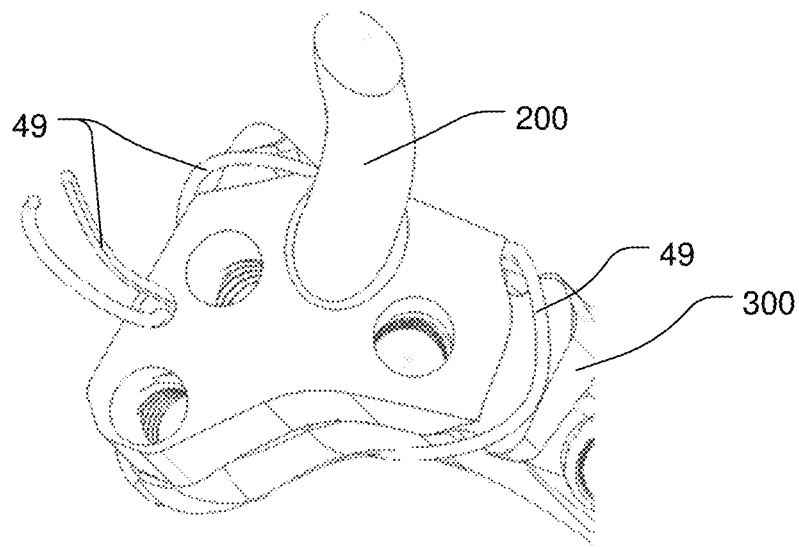
Fig. 10
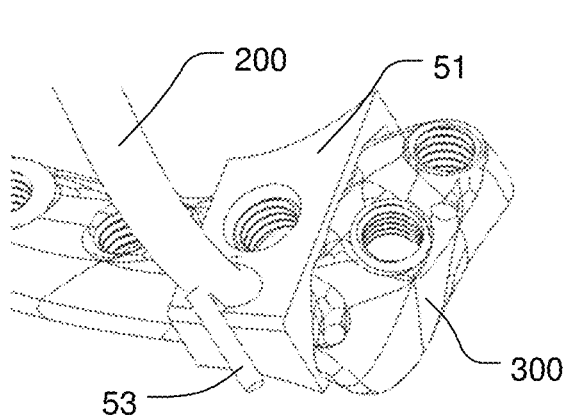
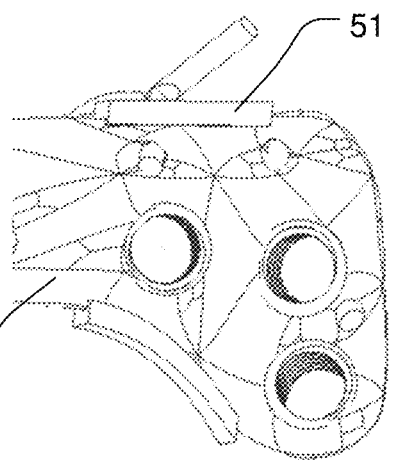
Fig. 11a  Fig. 11b

POSITIONING DEVICE FOR FIXING A POLYAXIAL PLATE TO A TUBULAR BONE USING A HOLE SECTION

FIELD OF THE INVENTION

The present invention relates to a positioning device for plate osteosynthesis.

BACKGROUND OF THE INVENTION

Plates are known aids for the treatment of fractures, for example of long tubular bones, but also of other bones. They are connected to the bone by screws.

In previously known plates, the screws are screwed into the bone through discrete openings in the plate in a predetermined position relative to the plate. The exact placement of the screws in the bones requires an extensive experience of the surgeon.

The object of the present invention is to propose a positioning device for fixing a bone using a plate.

SUMMARY OF THE INVENTION

The object of the present invention is achieved with a positioning device comprising a plate holder which connects the positioning device to a plate and/or to a bone.

The positioning device according to the present invention serves to position and/or to fix a plate to a bone. The positioning device comprises a plate holder. The latter comprises a first fastening device for its releasable fastening to the plate. Said plate holder comprises a second fastening device.

The positioning device according to the present invention also comprises a receptacle for an adjustment device. The adjustment device comprises at least one navigation device. The navigation device is designed to receive an interlocking device, such as a bone screw, and/or an instrument (e.g. tissue sleeve, drill sleeve, drill, screwdriver, depth gauge), at least in sections.

The receptacle comprises at least one or exactly one third fastening device or is connected thereto.

An element (or a fastening device) from the group consisting of the second fastening device and the third fastening device is designed as a hole section with a plurality of holes or comprises such a hole section.

The other element of the group is designed as an insertion section. The insertion section and the holes are designed to releasably connect the second fastening device to the third fastening device.

Thus, in an alternative, the plate holder comprises the hole section, whereas the receptacle comprises the insertion section. In the other alternative, the plate holder comprises the insertion section, whereas the receptacle comprises the hole section.

All of the embodiments disclosed herein are exemplary embodiments according to the present invention.

The present invention further encompasses any combination of the features disclosed herein, provided such a combination is not recognized by a person skilled in the art as being technically impossible.

In all of the aforementioned and following statements, the use of the expression "may be" or "may have" and so on, is to be understood synonymously with "preferably is" or "preferably has", and so on, respectively, and is intended to illustrate embodiments according to the present invention.

Whenever numerical words are mentioned herein, the person skilled in the art shall understand them as indication of a numerical lower limit. Hence, unless this leads to a contradiction evident for the person skilled in the art, the person skilled in the art will comprehend for example "one" as encompassing "at least one". This understanding is also equally encompassed by the present invention as the interpretation that a numerical word, for example, "one" may alternatively mean "exactly one", wherever this is evidently technically possible in the view of the person skilled in the art. Both of these understandings are encompassed by the present invention and apply herein to all numerical words used herein.

Subject-matters of the dependent claims are each also advantageous developments of the present invention.

In some embodiments, the plate holder has a handle section for the surgeon, preferably at one of its two ends.

In some embodiments, the holes have each a longitudinal axis. Not all longitudinal axes of the holes are parallel to each other. In some embodiments, five or more longitudinal axes are not parallel to each other.

In some embodiments, the holes are arranged in a row or on a straight line or on a curved or serpentine curve. In some embodiments, the holes are not arranged in several rows (each with more than one hole) next to one another. This allows a particularly clear and space-saving arrangement of the individual holes.

In some embodiments, the holes are arranged in—preferably only—one row or along—preferably only—one straight line or curve.

In some embodiments, the longitudinal extent of the holes arranged in a row or along a straight or curved line is at least 5 cm, 10 cm, 15 cm, 20 cm, 25 cm or has a different dimension. The first and the last hole for inserting the insertion section are, therefore, arranged at least 5 cm, 10 cm, 15 cm, 20 cm, 25 cm or any other dimension apart.

In some embodiments, a first number of holes is arranged in—preferably only—one row or along—preferably only—one straight or curved line. A second number of holes is arranged offset from the aforementioned row arrangement or from the aforementioned arrangement along a straight line or curve. For example, at least one, two or more holes are arranged in rows one behind the other at an angle relative to the longitudinal alignment of the first holes. The angle of the holes arranged in a row may be, for example, 30 degrees, 60 degrees, 90 degrees, 120 degrees or another number of degrees. The longitudinal extension of the first number of holes of the hole section of the holes arranged in a row or along a straight or curved line is, in some embodiments, at least 5 cm, 10 cm, 15 cm, 20 cm, 25 cm or has another dimension. For example, the first number of holes may be purely exemplarily three, five, eight, ten or any other number. The second number of holes may be purely exemplarily two, four, five or any other number. The arrangement of the second number of holes may correlate with an arrangement of holes in a plate for fixation to a tubular bone.

In some embodiments, at least one of the holes of the hole section comprises a rotation-stop. This serves to prevent rotation of an insertion section inserted in a hole.

The rotation-stop may be or may have an asymmetrical cross-sectional shape.

Alternatively or additionally, the insertion section inserted in a hole comprises a rotation-stop which is designed e.g. as stated above.

In some embodiments, the first fastening device of the plate holder comprises a cannulated screw and/or a screw with a longitudinal opening through the entire length of the screw or is connected thereto.

In some embodiments, the first fastening device of the plate holder comprises a screw and/or a section which is or will be form-fit connected to the plate.

In some embodiments, the cannulated screw and/or the screw with a longitudinal opening, which are designed, at least in section, as a funnel shape, is connected to a funnel arrangement or to a funnel-shaped extension or is arranged adjacent to it.

In some embodiments the hole section (second fastening device) is connected to the plate (here also: bone plate) via the cannulated screw, in other embodiments the hole section (second fastening device) is connected directly to the bone or to another implant, in particular releasably fixed, optionally blocking all degrees of freedom.

In some embodiments, the hole section is non-releasably connected to the receptacle or to the plate holder.

In some embodiments, the hole section is releasably connected to the receptacle or to the plate holder, wherein the receptacle, with regard to its longitudinal axis, is preferably arranged rotation-proof against or with respect to the hole section.

In particular, the above-mentioned releasable connection is a form-fit connection or fixation of the receptacle with the hole section.

In some embodiments, the form-fit connection or fixation is not a screw connection or comprises no screw connection.

The form-fit connection or fixation may be a plug-in connection, for example by inserting a shoulder of the receptacle into an opening of the hole section.

In some embodiments, at least one of the holes of the hole section comprises, or is connected to, a display device. The display device, which preferably does not operate electrically and/or is not connected to an electrical voltage source, is shiftable from a first position into a second position, for example by pressure or force.

In some embodiments, the display device is an optical display, for example designed as a viewing window with a color position behind it; when an end position of the insertion section is reached within a hole, for example, a colored marking may become visible as visual feedback.

In some embodiments, the display device is designed as a display or to display that the correct position of the receptacle for the adjustment device has been reached relative to the hole section, allowing the surgeon to safely insert and aim and place the instrument or screw in the hole of the plate or in the corresponding bone.

In some embodiments, the display device is designed as a display of a screw that has already been set/a hole that has already been drilled in the associated hole in the plate.

The display device serves the surgeons, in particular intraoperatively, in particular to display that a, for example the third, fastening device in the form of an insertion section has already been inserted through the hole in question.

In some embodiments, the display device comprises a, in particular longitudinally displaceable, section, for example a ring, which may be displaced from the first position to the second position.

In some embodiments, the display device comprises at least two or three different colors. Hereby, red and green may facilitate the orientation of the surgeons in a particularly simple or intuitive way.

The display device, in particular the colored one, may be such that a marking, for example a colored marking (e.g. in green) is visible to the surgeon as long as no insertion section has been inserted into the hole in question, and that the marking is no longer visible if or once this has changed.

It may also be provided that a first marking (such as a color marking, e.g. a green one) is visible as long as no insertion section has been inserted in the relevant hole and that, after an insertion section has been inserted, a second marking (such as another color marking, e.g. a red one) is visible instead of the first marking.

The display device could also be designed to be actuated by the instrument or by hand in one work step, for example by inserting, folding, countersinking, twisting, etc., of pins, flags, cones, etc. Such elements may be included.

A membrane that is pierced also counts as a display device in some embodiments. If it is pierced, it indicates that an insertion section has been inserted into the corresponding hole, otherwise not. Such a membrane or a plurality of such membranes may be part of the positioning device.

In some embodiments, the plate holder has at least one through-opening for the passage of a surgical wire and/or a Kirschner wire.

In some embodiments, the positioning device also comprises a support device. The latter may preferably be releasably connected to further sections of the positioning device by the hole section, e.g. by being insertable into one of the holes of the hole section using a separate insertion device of the support device.

The support device may be used to support a form-fit and/or force-fit support of the positioning device on, by and/or above the plate. This ensures or facilitates an accurate functioning of the positioning device and in particular an accurate alignment of the holes in relation to the associated through-openings of the plate.

The support device may also be provided to rest on the patient's body surface or skin.

In some embodiments, several supporting devices are provided, which may be of the same or different design.

In some embodiments, the support device comprises a through-opening for the passage of a rod or another element, with or without a tissue protection sleeve. The support device may comprise a fixing device for fixing the rod or another element or the tissue protection sleeve. The fixing device may be, for example, a screw, an eccentric or the like.

In some embodiments, the plurality of holes is marked distinguishable from each other, in particular to distinguish them optically during the operation.

In some embodiments, the first fastening device comprises a clamping section or section with clamps and/or a pin.

In some embodiments, the first fastening device has a wire section.

In some embodiments, the positioning device further comprises one or more locking devices or latching devices. They are each assigned to one or more of the holes. They releasably latch the insertion section or an end section thereof in the respective hole. In this, a snap-in nose and a snap-in step or snap-in opening may be provided. The snap-in nose may be provided on the second or third fastening device and the snap-in step or snap-in opening may be provided on the other of the two fastening devices, respectively.

In some embodiments, the positioning device comprises, in addition to or instead of, the locking or latching devices at least one device which functions by self-locking, e.g. by eccentric force application.

Latching devices may prevent the second fastening device from accidently slipping out of the third fastening device (or vice versa) during use of the positioning device. Nevertheless, the snap-in connection may be easily released by the surgeon. An operating element may be provided for this purpose. However, the snap-in connection may also be designed so that it may be released by pulling.

In some embodiments, the plate holder ends at both its ends with the first fastening device or with the second fastening device, or they lie in the end regions thereof.

In some embodiments, the adjustment device is a component of the positioning device that is movable or shiftable relative to the receptacle. The adjustment device may be rotated, for example, by a sliding friction movement in a ring of the receptacle. The adjustment device may be moved relative to the receptacle optionally continuously or stepless or by a snap-in movement. The adjustment device may be lockable or fixable relative to the receptacle, for example by a clamping device.

In some embodiments, the navigation device may be moved in the receptacle by the adjustment device. In particular, the navigation device may be hollow and continuous on the inside (cylindrical), so that, for example, a tissue protection sleeve and/or an instrument, in particular a drill, may be inserted or plugged into the navigation device. Using the navigation device, an instrument may be aligned with an intramedullary nail, a plate or another (bone) implant. The navigation device may be a receptacle for an instrument.

In some embodiments, the receptacle is one-piece or integral with the hole section.

In some embodiments, the second fastening device of the plate holder has a cross-section that is rectangular, non-round, non-circular, angular, triangular, etc. The cross-section may be a combination of a round shape and a square shape and may have, for example, the cross-sectional shape of a "D". The cross-sectional shape may preferably be advantageous to allow a clear alignment between the second and the third fastening device, be easy to insert and/or ensure high rigidity and accuracy of fit.

In some embodiments, the second fastening device or the third fastening device comprises at least one step or a stop, which limits further or deeper insertion of the fastening device provided with the step or the stop into the respective other fastening device (i.e. into the third or the second).

In some embodiments, the hole section is designed and/or arranged in such a way that an insertion section is inserted into the holes of the hole section "from below" and/or from the side of the hole section facing the plate during use.

In some embodiments, the second fastening device is not a screw connection or comprises no screw connection.

In some embodiments, the upper edges and/or lower edges of all or some (preferably at least five) holes in the hole section end with the upper edge and/or lower edge of the hole section. In these embodiments, these holes do not protrude above the upper and/or lower surface of the hole section which touches or surrounds them. With this design, the holes may advantageously be easily manufactured and the hole section may advantageously be easily cleaned.

In some embodiments, some or all of the holes of the hole section are through-openings. In others they are blind holes, positioning aids, notches, fits, or the like. Preferably the holes are receptacles, especially for at least one insertion section, preferably these receptacles are designed according to one of the above-mentioned designs. The hole section therefore need not have any holes. In certain embodiments it comprises blind holes, positioning aids, notches, fits or similar. The hole section is preferably a receiving section for receiving at least one insertion section.

In some embodiments, the insertion section is a fixable carriage or a sliding carriage.

In some embodiments, the hole section is a rail or a, preferably slotted, profile.

In some embodiments, the hole portion and the receptacle for the adjustment device form a structure with a closed periphery. This structure can circumscribe a through-opening. In this way, the rigidity of the positioning device and in particular of the hole section may be advantageously increased.

Several, some or all of the fastening sections mentioned herein may be connecting or joining sections. These two terms (fastening section on the one hand and connecting or joining section on the other) can therefore be used synonymously.

In some embodiments, the first fastening section and/or a screw used in or with it comprises a device to prevent rotation between the plate and the plate holder. This device may be one-piece or multi-piece. It may be or comprise a centering device. It may comprise at least a second screw, a pin, a stop or the like, respectively.

In some embodiments, the hole section has markings of holes arranged on the top or on the side of the hole section facing away from the plate in use.

In some embodiments, the receptacle, a web connected to it and an insertion section which is in turn connected to the web and is designed as a third fastening device are one-piece.

In some embodiments, the plate holder has one or more undercuts in which one or more sections of the plate are received during use. The undercuts may be arranged in the region of the first fastening device or may be part thereof.

In some embodiments, the hole section and/or several or all of its holes do not have sleeves.

In some embodiments, the positioning device has no socket arrangement and/or is not connected to one.

In some embodiments, the positioning device does not have a plug-in section with which a guide arch would be connected with a socket arrangement and/or with sleeves.

In some embodiments, the positioning device does not have a guide arch.

In some embodiments, the plate holder is not screwed to the hole section. Optionally the plate holder is rather integral or in one piece with the hole section. For this purpose, the holes may be manufactured in a simple manner, for example by punching, laser cutting, etc., them into the material of the plate holder.

In some embodiments, the plate holder and/or the hole section is multi-part, designed e.g. as a modular system. This allows different plate systems (e.g. for tibia, femur, humerus or other bones) and/or different plate lengths (e.g. with seven holes, with nine holes or more) and/or designs (e.g. a left and a right variant) to be served.

In some embodiments, the positioning device is connected to a plate for osteosynthesis, the plate having a plurality of through-openings for receiving one or more interlocking devices. The depth of the through-openings corresponds respectively to a thickness of the plate, whereby a plurality of the holes is each assigned to one of the through-openings, e.g. exactly one hole (or several) to exactly one through-opening (or several).

In some embodiments, the adjustment device is designed such that the navigation device received in the adjustment device is aligned and movable in such a way that an interlocking device or an instrument received in the navigation device is movable, in particular circumscribing or within a cone surface. In particular, the cone tip comes to rest within the depth of the through-opening of the hole into which the insertion section is inserted.

In some exemplary embodiments according to the present invention, the positioning device may be denoted as monoaxial if the positioning device is designed or set to insert the interlocking device, e.g. a bone screw, at only one angle into the specific through-opening of the plate.

The plate may be designed polyaxial or monoaxial, or as a combination thereof. The same may apply to the positioning device according to the present invention.

"Polyaxial" may be understood to mean that the positioning device connected to the plate is designed or set to insert the interlocking device, e.g. a bone screw, at a variety of angles, also called multidirectional, into a specific through-opening in the plate.

"Monoaxial" may be understood to mean that the positioning device connected to the plate is designed or set to insert the interlocking device, e.g. a bone screw, at only one angle into a specific through-opening in the plate.

In some exemplary embodiments according to the present invention, the plate may be denoted as polyaxial if the positioning device is designed or set to insert the interlocking devices, e.g. bone screws, into the plate at more than one angle.

In some exemplary embodiments according to the present invention, the cross-sectional shape of some of the holes or of the holes is oval, rectangular, non-round, non-circular, angular, triangular, etc. They may be designed as a combination of a round shape and a square shape and have for example the cross-sectional shape of a "D". The cross-sectional shape may advantageously allow a clear alignment, be easy to insert and/or ensure high rigidity and accuracy of fit.

Preferably, the tip of the virtual or arithmetically determinable cone comes to rest on a longitudinal axis of the corresponding through-opening, e.g. in the center of the hole when the through-opening is viewed from above.

Whenever cone is mentioned here, this should not be limiting. A "cone tip" may also be understood to mean the intersection of two or more insertion directions, which may be achieved by moving the interlocking device by the adjustment device. An actual cone shape is not essential here.

The cone may also be limited to a cutout/section in one or more directions, e.g. it may have an annular circumference that is not continuous. In this way, e.g. collisions may be advantageously avoided or critical anatomical structures (nerves, vessels, . . . ) may be spared.

The cone tip may optionally be movable/pivotable to the plate, e.g. along an elongated hole on the bone plate.

One or more of the holes of the plate may be an elongated hole, and/or a hole that does not have a round cross-section.

The positioning device according to the present invention may be used for minimally invasive insertion of the plate at a bone.

At least plate and plate holder may be made of radiopaque materials, optionally also other or all other elements of the positioning device.

Individual elements or sections of individual elements can carry X-ray markers to make them visible in the X-ray process. Thus, this is particularly advantageous for displaying their positions and/or angles and/or orientation absolutely or relative to each other or to the plate or to an anatomical structure (e.g. bone, nerve, vessel, . . . ).

In some embodiments, it is intended to align one hole of the hole section with several through-openings of the plate. In this case—or independently thereof—the navigation device may be designed to be pivotable with respect to the hole section. An optional grid arrangement could facilitate or enable this. An advantage that may be achieved in this way may be that only one hole in the hole section is required for equipping or machining a plurality of through holes. The hole section may thus be designed smaller, lighter and clearer.

In some embodiments, some (preferably at least five) or all of the holes in the hole section do not have a slotted edge.

In some embodiments, the hole section is not provided to be connected (directly or indirectly) to both the plate holder and the receptacle by insertion and/or screwing.

In some embodiments, the hole section is not connected (directly or indirectly) to both the plate holder and the receptacle by insertion and/or screwing.

In some embodiments, the hole section is not screwed to the plate holder.

In some embodiments, the hole section is screwed in one piece or integrally to the plate holder. This may advantageously prevent an unwanted relative movement, for example in a screw connection (which is not present here).

In some embodiments, the hole section has not only holes in, or essentially in, the longitudinal direction of the hole section, but also holes that are offset transversely with respect to the longitudinal direction of the hole section. By these offset holes, plates may advantageously also be fixed and screwed, which likewise have holes which are offset transversely with respect to the longitudinal direction of the plate.

In some embodiments, the offset holes of the hole section form a row of holes arranged one behind the other. In this embodiment, the angle of the straight line on which this row lies, related to the longitudinal orientation of the hole section, has purely exemplarily a value between 45 and 135 degrees, particularly preferably between 50 and 90 degrees, very particularly preferably 60 degrees.

In some embodiments, at least one hole, several arbitrary holes or all holes of the hole section are designed to be rotation-proof. A rotation-proof design does not allow rotation of, for example, an insertion section, a pin or a third fastening device about its longitudinal axis. A rotation-proof design may have, for example, a hole cross-sectional shape with an asymmetrical, non-circular, oval, U-shaped, polygonal (e.g. inner triangular, inner square, Allen screw) and/or inner hexalobular shape. The element to be inserted may have a corresponding cross-sectional shape.

In some embodiments, at least one hole, any number of random holes, or all holes of the hole section are optionally not provided and designed to receive a navigation device or a tissue protection sleeve. The cross-section and/or the diameter of the respective hole on the one hand and of the navigation device and/or the tissue protection sleeve on the other hand may differ from each other.

In some embodiments, the longitudinal axes of the holes of the hole section of at least two holes are arranged parallel or non-parallel to one another.

In some embodiments, the upper stop surface or the upper edge of at least a first hole of the hole section lies at a different height on the hole section and/or relative to the hole section than the upper stop surface or the upper edge of at least a second and/or a third hole of the hole section. Such different heights may ensure an identical distance between holes of the hole section and associated holes of the plate. In addition, different heights may help ensure that holes in the plate may be accessed through different holes in the hole section using different instrumentation, even if the different instrumentation requires different distances between the hole in the hole section and the hole in the plate.

In some embodiments, the hole section—directly or indirectly, respectively—is not connected to the plate holder, in particular releasably, by a fastening device, and at the same time is connected to the receptacle for the adjusting device by another fastening device, in particular releasably.

With the last related embodiments, connection work (screws, plugging in, etc.) may be advantageously saved. In addition, the play that is created due to connecting is advantageously reduced. The lower modularity resulting from the omission of connecting sections is accepted for this purpose.

Some or all of the embodiments according to the present invention may have one, several or all of the advantages mentioned supra and/or below.

Using the positioning device according to the present invention, minor misalignments during the positioning and/or screwing (so-called "setting") of interlocking screws into a plate may advantageously be corrected during an operation.

Using the positioning device according to the present invention, misalignment of the plate or the implant or misalignment of the bone may be advantageously corrected by inserting an interlocking screw and subsequently repositioning (the so-called "corrective or transposition osteotomy") through or by the plate during surgery.

The position and angle of bores for the interlocking screws and their position may advantageously be still adapted intraoperatively to an individual situation, anatomical situation and/or a situation resulting from an injury by the positioning device according to the present invention.

Furthermore, the angle of the interlocking device penetrating the plate (herein: interlocking screws, Kirschner wire, etc.) or instruments (herein: drill, trocar, measuring rod, etc.) may be advantageously varied intraoperatively using the positioning device according to the present invention in order to, for example, reposition fracture fragments, adapt them anatomically correctly, or reposition the bones in relation to each other within the scope of a corrective osteotomy.

According to the present invention, the positioning device may be securely and easily releasably connected to the plate to be fixed. The positioning device may thus be decoupled and removed from the fixed plate. The positioning device according to the present invention may advantageously ensure that the positioning device, advantageously, does not rotate relative to the plate during screwing, or during loosening of the screw connection, between bone and plate.

According to the present invention, the positioning device may offer the possibility of a minimally invasive implantation of polyaxial osteosynthesis plates. Using the positioning device, the surgeon may align the navigation device with one or more specific through-openings, even if he cannot see them and cannot see the plate itself as well, due to the minimally (invasive) access. The surgeon may use fluoroscopy or x-ray, but this is left at his own discretion.

The positioning device may be handled intuitively. To move the instrument within the positioning device, advantageously only one step is required, namely replugging the insertion section from one hole to another.

A display device, optionally in combination with a marking, may be advantageous for the surgeon in facilitating the orientation for addressing the desired through-openings for the interlocking screws, in particular during the minimally invasive implantation.

The positioning device may advantageously enable a safe limiting of the angle when inserting the interlocking screws into the through-openings and may thus prevent collisions of interlocking screws or of interlocking screws with an instrument, in particular, a drill.

The positioning device may enable a safe limiting of the angle when inserting the interlocking screws into the through-opening and may thus ensure a firm, angle-stable locking of the interlocking screws in the plate.

If multiple receptacles, as encompassed by some embodiments, are used simultaneously, fragment movement may be facilitated.

Advantageously, increased stabilization may be achieved by using several receptacles at the same time.

Visual feedback regarding the alignment of the navigation device may also be advantageous.

In addition, the present invention allows simple, angle-stable locking of the bone screws/screw in the bone plate (plate)/implant.

The present invention is exemplarily explained below with reference to the accompanying figures, in which identical reference numerals refer to identical or similar components. In the schematically simplified figures:

BRIEF DESCRIPTION OF THE DRAWINGS

FIG. 9*a,b* show a cannulated screw as an optional design of the first fastening device of the plate holder with the plate;

FIG. 10 shows a wire connection as an optional design of the first fastening device of the plate holder with the plate;

FIG. 11*a,b* show a clamping device with an interlocking pin as an example of a first fastening device of the plate holder with the plate;

DETAILED DESCRIPTION OF THE EMBODIMENTS

Figure 1:
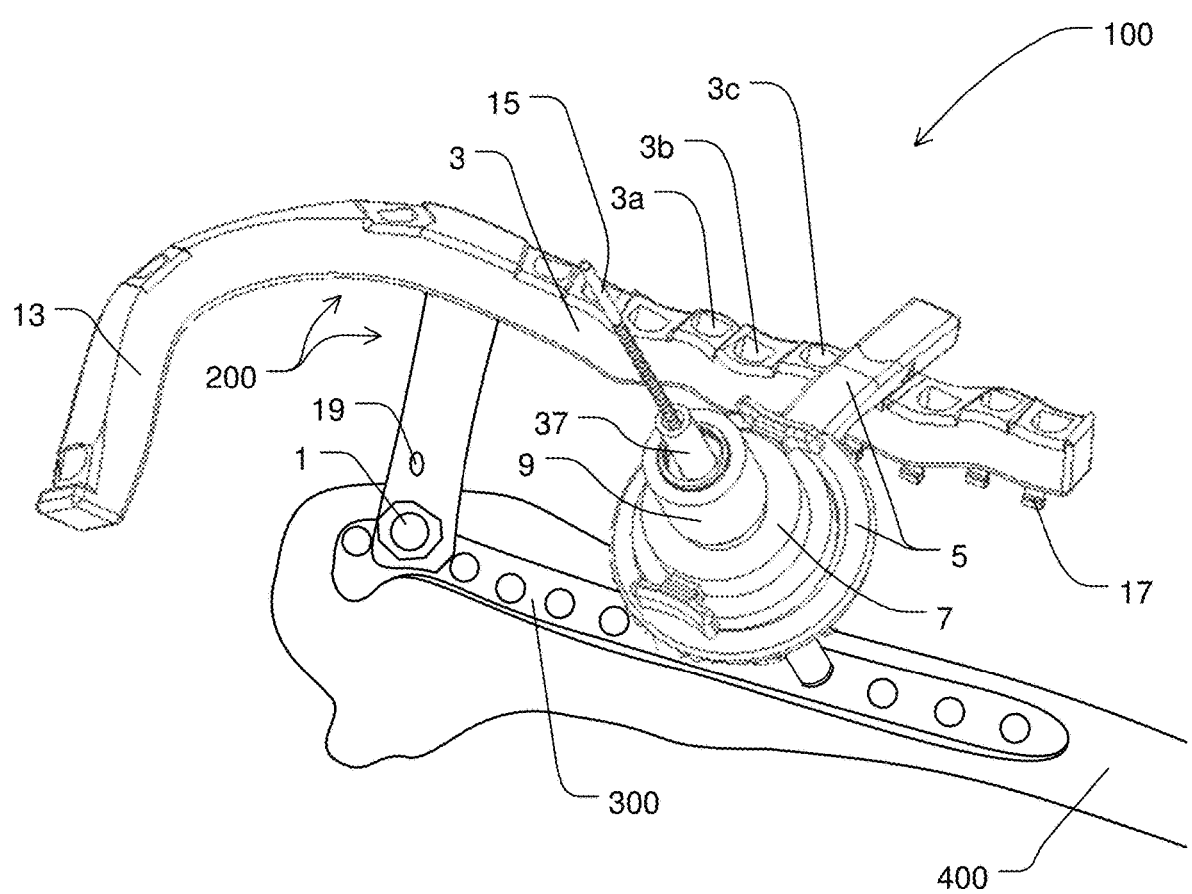
FIG. 1 shows a perspective view of a positioning device according to the present invention in a first exemplary embodiment, connected to a plate and to a bone.

FIG. 1 shows a positioning device 100 according to the present invention in a first exemplary embodiment. The positioning device 100 comprises a plate holder 200 which connects the positioning device 100 to a plate 300 and/or to a bone 400. The connection is optionally made by an optionally cannulated screw 1 as a first fastening device (see FIGS. 9*a* and 9*b*). The bone 400 is purely exemplary a tibia bone.

The plate 300 is connected e.g. to the bone 400 by screw connections in order to stabilize a previous bone fracture and to support the healing process. The positioning device 100 according to the present invention serves to position the corresponding screws (which are not shown in FIG. 1) precisely in the preferably polyaxially arranged holes 301, 303, 305, 308 (see FIG. 5e; in other figures, these reference numerals are, for the sake of clarity, not shown, but the holes nevertheless exist) of the plate 300.

In this embodiment, the plate holder 200 comprises a hole section 3 optionally designed as a second fastening device. The hole section 3 may be embodied integrally with the connecting web or with other sections of the plate holder 200 to the (here: cannulated) screw 1, for example by a clamp connection, a solder connection, an adhesive connection, a screw connection, a plug connection or another connection.

The hole section 3 comprises a plurality of holes 3a, 3b, 3c (and further holes which are not individually numbered for better clarity) for connection to a receptacle 5 for an adjustment device 7 with a navigation device 9. The receptacle 5 comprises a web and an insertion section 11 designed as a third fastening device, which may be referred to as a pin (see FIGS. 3a and 3b). The insertion section 11 is inserted into one or successively into several of the holes 3a, 3b, 3c of the hole section 3.

Furthermore, the plate holder 200 in this embodiment has a handle section 13 with which the positioning device 100 may be manually guided, aligned and held.

A tissue protection sleeve 37 and an instrument 15, which may be, for example, a drill for drilling in the bone 400, are introduced into the navigation device 9 purely exemplarily. Subsequently, the plate 300 may be connected and fixed to the bone 400 using screws which are screwed into the drilled bores.

At hole section 3, purely exemplarily, small foldable shoulders 17 may be arranged, which may display, as a display device, a processing state of the drillings or screw connections in the bone 400. In the open, not folded state, for example a screw that has not yet been inserted or a drilling that has not been completed is displayed. In the closed, folded state, e.g. an inserted screw or a completed drilling is displayed. This may be advantageous for the user in order to achieve the complete screwing of the plate as quickly as possible. Differently designed display devices, as well as no devices, may be provided.

The holes 3a, 3b, 3c have an asymmetrical cross-sectional form (with reference to FIG. 1, said form optionally has a flat, rear-side bore wall), so that the insertion sections 11 cannot twist or rotate in the holes 3a, 3b, 3c.

Above the cannulated screw 1, the plate holder 200 comprises an optional through-opening 19 into which a so-called surgical wire, K-wire or Kirschner wire may be inserted.

Figure 2A:
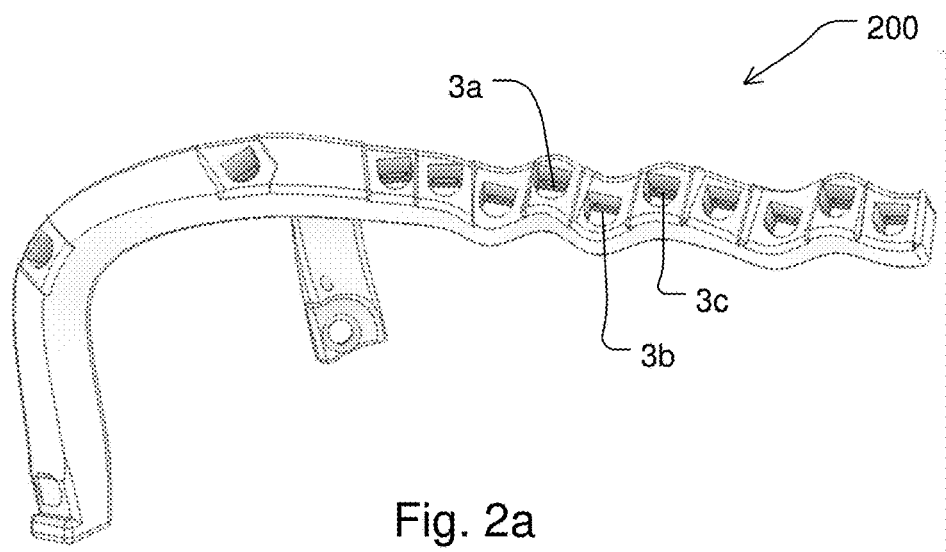
FIG. 2*a-c* show different perspective views of a plate holder of the positioning device according to the present invention shown in FIG. 1.
Figure 2B:
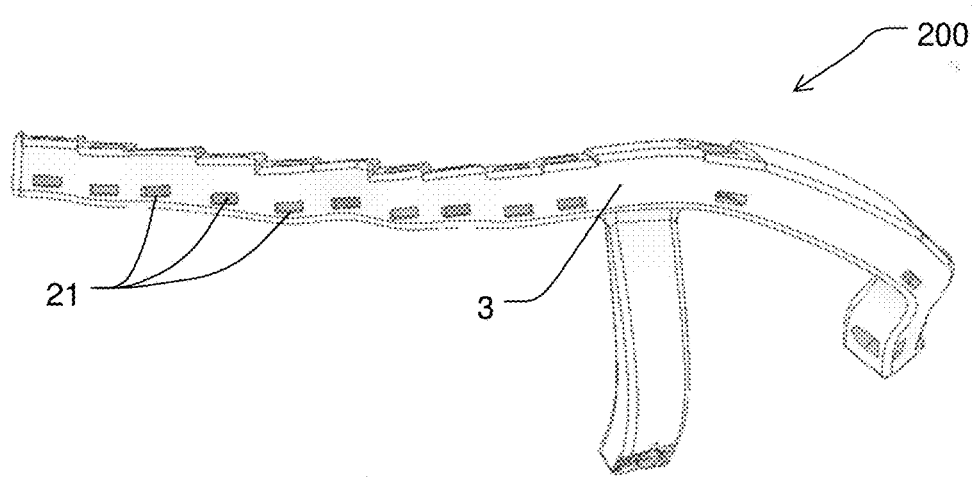
Figure 2C:
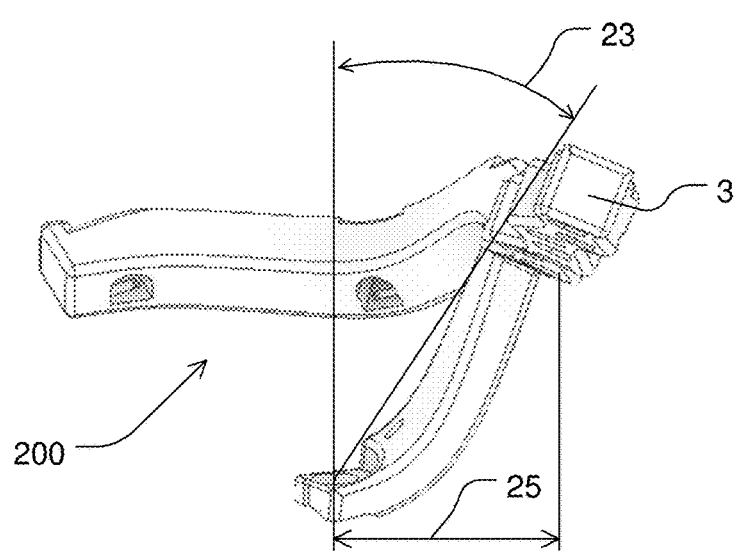

In FIGS. 2a, 2b and 2c, the plate holder 200 of the positioning device 100 according to the present invention is shown in different perspective views.

FIG. 2b shows optionally rectangular recesses 21, which are optionally provided for locking the inserted receptacle 5 (see FIG. 1). By this locking, the user may be given an optical, tactile and/or acoustic feedback about reaching the correct and final position of the insertion section 11 of the receptacle 5 in one of the holes 3a, 3b, 3c etc. of the hole section 3.

In FIG. 2c, the angle 23 and the lateral offset 25, or the corresponding shape of the plate holder, enable a chamfered reception of the navigation device 9 with respect to the longitudinal axis of the connection between plate holder 200 and plate 300. This may be advantageous for the user and may provide an increased overview of the plate 300 and the entire surgical area.

Figure 3A:
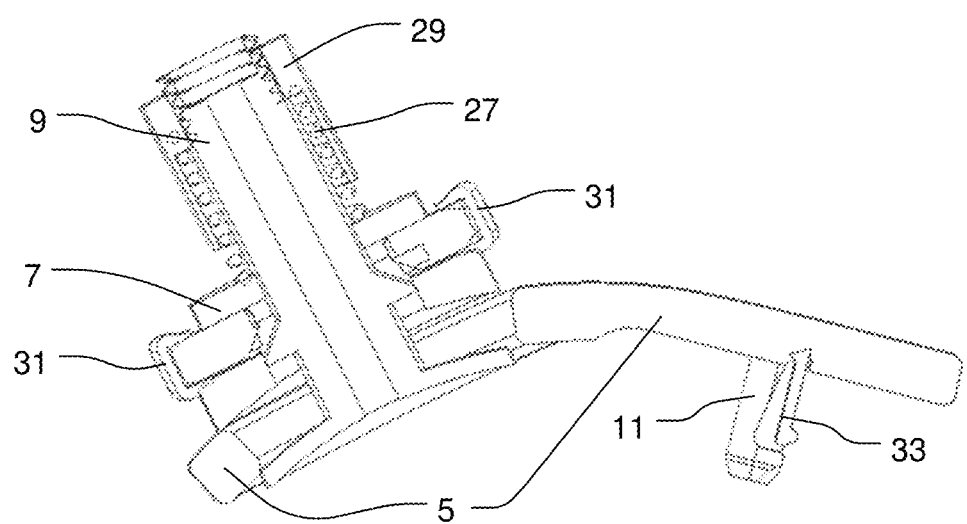
FIG. 3*a-c* show a receptacle with a fastening device, an adjustment device and a navigation device of the positioning device according to the present invention shown in FIG. 1.

FIG. 3a shows a side view of a receptacle 5 with a sectional view of the adjustment device 7 and the navigation device 9. An optional spiral spring 27 is arranged concentrically around the navigation device 9. The spiral spring 27 is inserted into an optional sleeve 29, which may be designated as a nut. The sleeve 29 is both a protection against unintentional jamming of possible components in or on the spiral spring 27 as well as a protection against contaminations or injuries. The spring pre-tension of the spiral spring 27 may be and/or will be adjusted and pre-tensioned by axial compression relative to the longitudinal axis of the spiral spring 27. By optional actuating pins or elements 31 and optional inclined planes arranged radially further inward towards the longitudinal axis, the spiral spring 27 may be compressed and simultaneously the pressure on an optional intermediate ring between the actuating pins 31 and the receptacle 5 may be relieved. Thus, this allows the adjustment device 7 to be moved easily or freely within the receptacle 5 and the navigation device 9 to be aligned onto the through-openings through the plate 300 into bone 400. After the adjustment, the actuation pins 31 are released again or shifted outwards. As a result, the spring force of the spiral spring 27 acts again on the intermediate ring and fixes or clamps the adjustment device 7, so that the drilling or screwing in the bones 400 may be carried out in an exact position.

As already described for FIG. 1, the holes 3a, 3b, 3c of the hole section 3 have an asymmetrical cross-sectional shape. Accordingly, the insertion section 11 optionally also has such an asymmetrical cross-sectional shape. A clear alignment, simple insertion and high rigidity and fitting accuracy of the receptacle 5 may thus advantageously be achieved.

Furthermore, the arrangement has an interlocking, which may be referred to as a latching device 33. The latching device 33 may be designed, for example, as an elastic plastic hook, which may be referred to as a snap-hook. A corresponding unlocking device by a slide or the like may additionally be arranged at the receptacle 5. This latching device 33 may advantageously prevent the receptacle 5 from accidentally slipping out during use of the positioning device. Furthermore, a clear and defined position of the navigation device 9 in the receptacle 5 or in relation thereto is possible using the latching device 33.

Figure 3B:
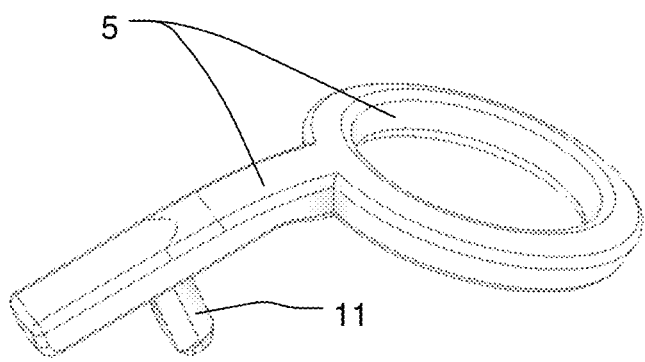

FIG. 3b shows the receptacle 5 with the insertion section 11 in a perspective view.

Figure 3C:
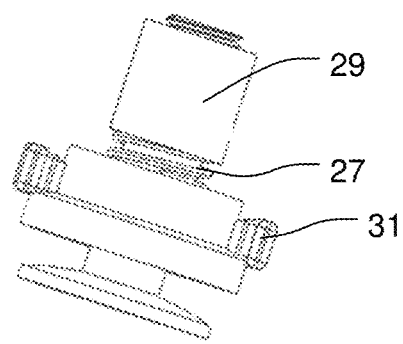

FIG. 3c shows the half-sectional view of the adjustment device 7 shown in FIG. 3a, of the navigation device 9 with further components in a side view.

Figure 4A:
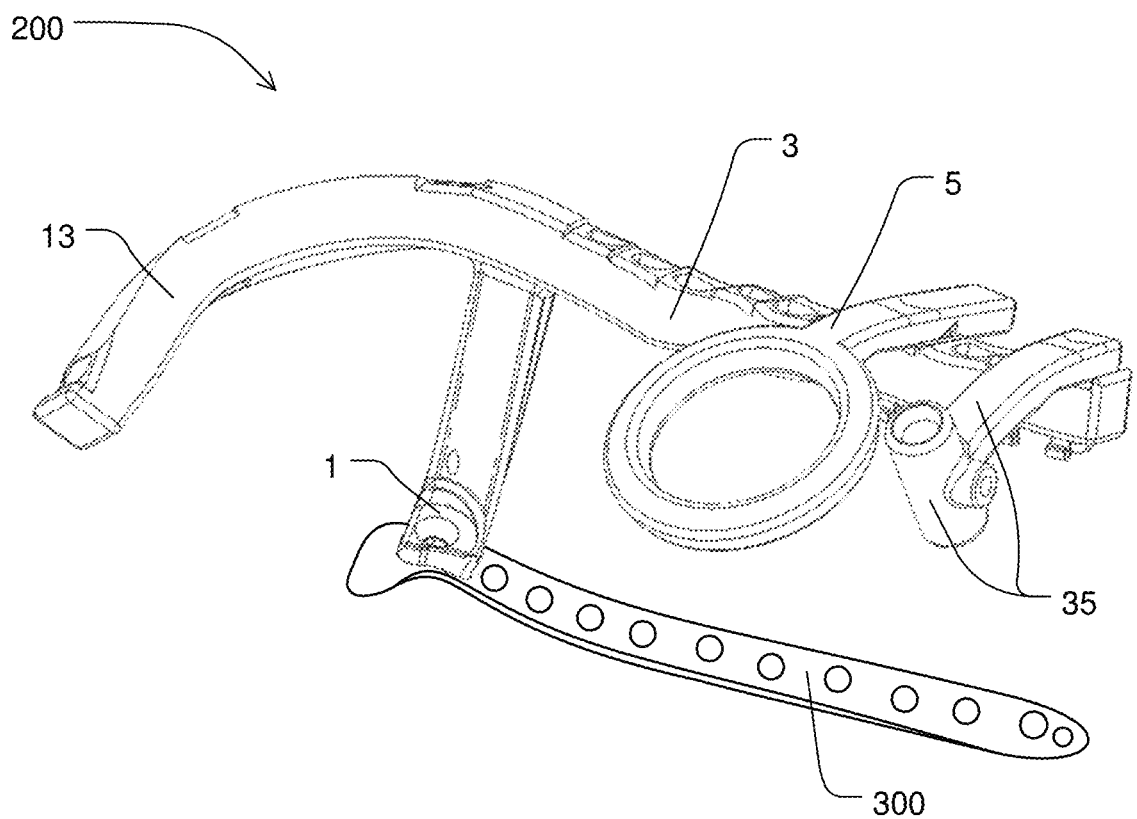
FIG. 4*a,b* show the plate holder, the plate, the receptacle of FIG. 1 and additionally a supporting device.

FIG. 4a shows the plate holder 200, the plate 300, the receptacle 5 and an optional support device 35. A tissue protection sleeve 37 (see FIG. 4b) and within this tissue protection sleeve 37a rod (not shown in FIGS. 4a and 4b) may be inserted into this support device 35 to support against plate 300. This may be necessary and advantageous if the embodiment of hole section 3 has numerous holes 3a, 3b, 3c, as shown here, resulting in a relatively long hole section 3. If drilling is then carried out at a hole that is far away, relative to the distance between the connecting web of the plate holder 200, which receives the cannulated screw 1, and the hole, this may lead to inaccuracies and collisions of the instrument/screw and plate due to the leverage effect when a force is applied to the holder 5 during drilling. However, inaccuracies should be avoided at all costs in order to achieve a high and accurate plate stability on the bone.

Collisions cause unwanted abrasion and should therefore also be avoided. Therefore, a support of the plate holder 200 may be achieved by the support device 35 and a rod inserted into it and an accurate drilling is possible.

The support device 35 may optionally be used as a receptacle 5. In this case, the support device 35 may have, for example, a navigation device 9 (instead of a tissue protection sleeve 37).

Figure 4B:
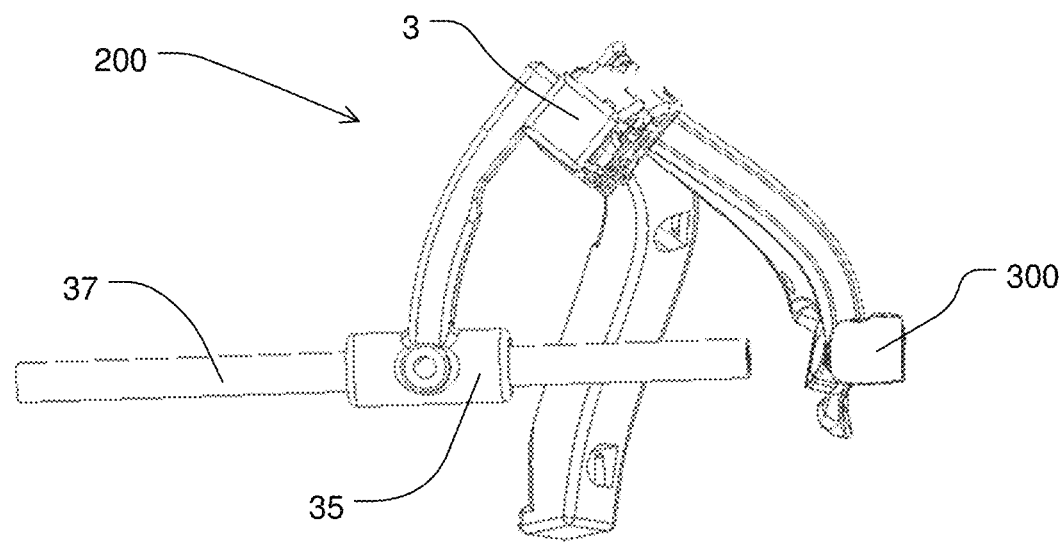

FIG. 4b shows a similar arrangement to the one shown in FIG. 4a, in another, perspective view, supplemented by the tissue protection sleeve 37, and without receptacle 5.

FIG. 5a to FIG. 5e show a further, second embodiment of the positioning device 100 according to the present invention compared to the first embodiment of FIGS. 1 to 4.

Figures 5A, 5B:
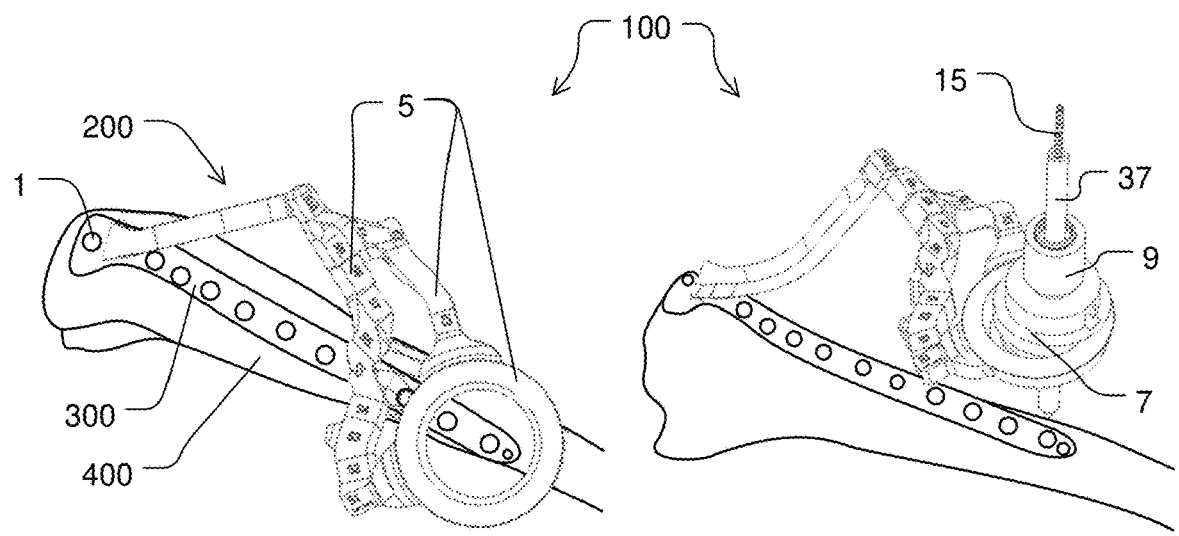
FIG. 5*a-e* show different perspective views of a positioning device according to the present invention in a second exemplary embodiment.

FIG. 5a shows the positioning device 100, connected to the plate 300 and to the bone 400. The connection is implemented by the cannulated screw 1 as a fastening device.

In this second embodiment, receptacle 5 additionally comprises, in an integral design, holes as a third fastening device, here as recesses 39, which are selected according to the hole to be drilled and are put on or connected to an insertion section as a second fastening device, here as a plug-in pin 41. The recesses 39 are concealed and not visible in the view of FIG. 5a and only clearly visible in FIG. 5c. The plug-in pin 41 is also not visible in FIG. 5a and clearly illustrated in FIG. 5e.

For better orientation of the surgeon, the recesses 39 are marked on the upper side, being visible in FIG. 5a, with markings S1 to S10 and K1 to K3, in order to give a clear assignment to the holes to be drilled in the bone 400 and to the screw fixing of the plate 300.

FIG. 5b shows the arrangement from FIG. 5a, supplemented by the adjustment device 7, the navigation device 9, the tissue protection sleeve 37 and the instrument 15. The description given for FIG. 1 and FIG. 5a applies analogously to FIG. 5b.

Figures 5C, 5D:
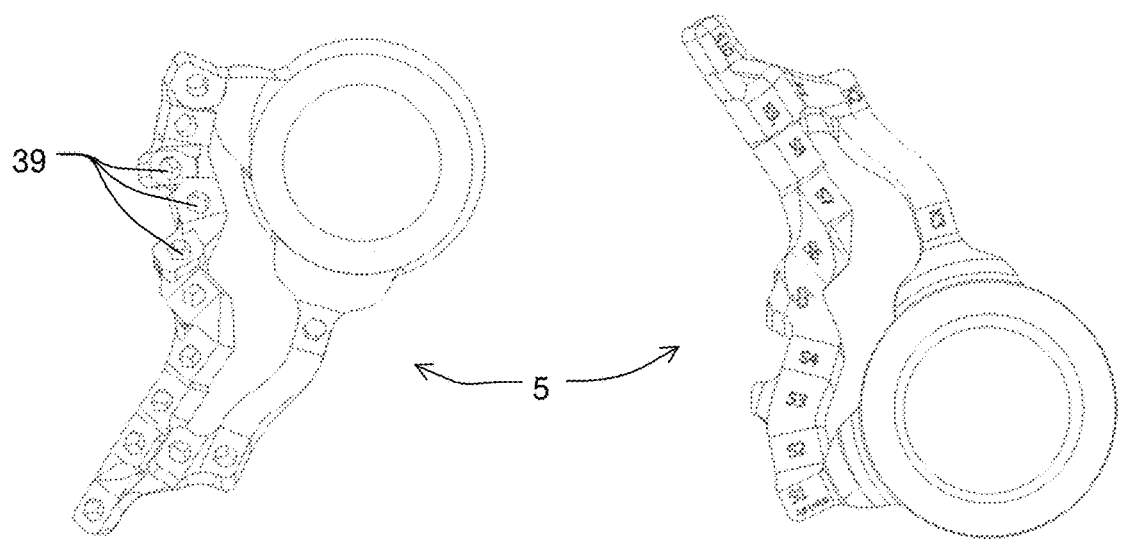

FIG. 5c shows the receptacle 5, rotated by 180 degrees relative to the view in FIG. 5a, so that the recesses 39 for connecting or inserting on the plug-in pin 41 are visible.

FIG. 5d shows the receptacle 5 in the view from FIG. 5a.

Figure 5E:
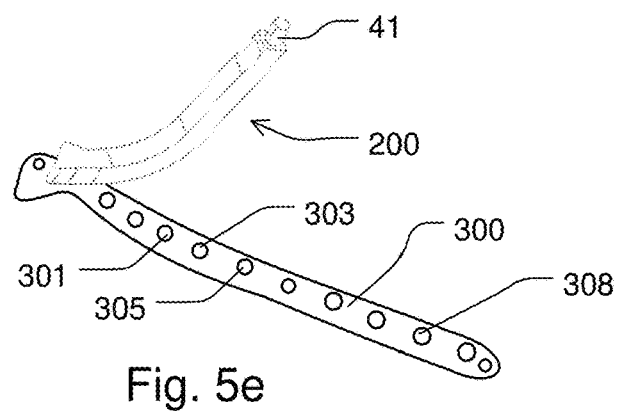

FIG. 5e shows the plate holder 200 with the plug-in pin 41. The plate holder 200 may be connected to the plate 300 by the cannulated screw 1 (see FIGS. 9a and 9b).

Figure 6:
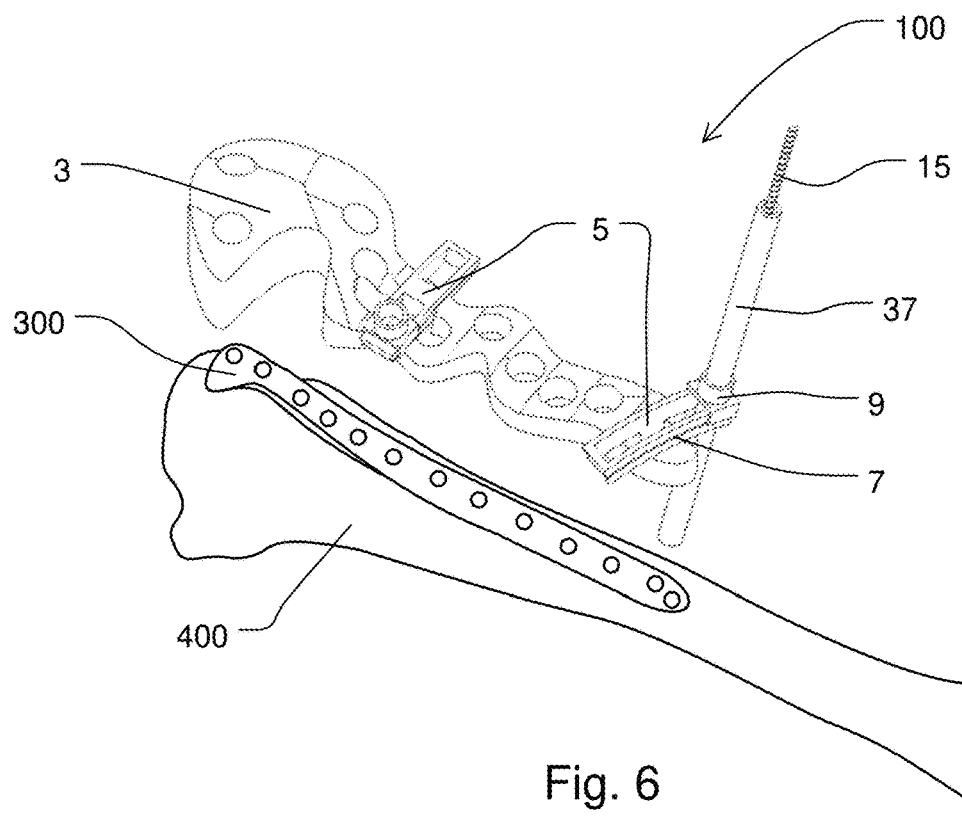
FIG. 6 shows a positioning device according to the present invention in a third exemplary embodiment.

FIG. 6 shows a positioning device 100 according to the present invention in a third exemplary embodiment. The plate holder 200 is not shown. Similar to the first embodiment shown in FIG. 1, the hole section 3 comprises holes for inserting the receptacle 5. The receptacle 5 has been greatly simplified compared to the first and second embodiments. The receptacle 5 and the adjustment device 7 have been functionally integrated into one component. The navigation device 9 may be moved in the adjustment device 7. The receptacle 5 or the adjustment device 7 may be rotated in the holes of the hole section 3. Using these two degrees of freedom, the instrument 15 may be aligned in the tissue protection sleeve 37 to the corresponding holes in the plate 300 and drilled into the bone 400.

Figure 7:
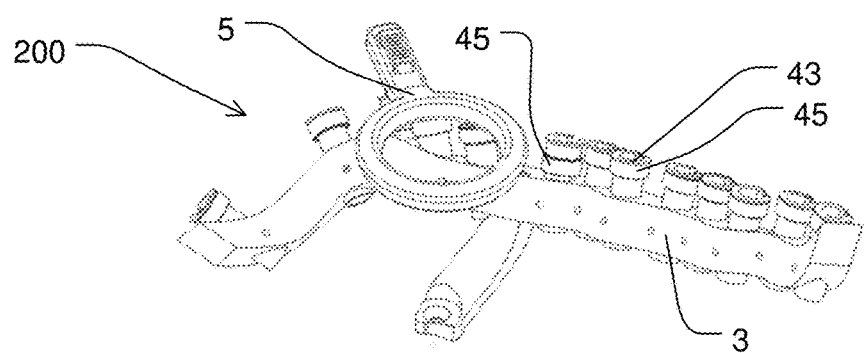
FIG. 7 shows the plate holder with a display device in an exemplary design.

FIG. 7 shows the plate holder 200 (as it was exemplarily shown in FIG. 2) with a display device designed in the form of optional rings 45. The rings 45 are elements which may be moved axially (in the longitudinal direction of the holes) and which may optionally be designed as sleeves or rings. If the receptacle 5 is inserted into the ring 45 and thus into the corresponding hole in the hole section 3, the ring 45 moves from top to bottom (based on the view in FIG. 7). This ring position is retained even if the receptacle 5 is pulled out again after drilling into the bone 400. Thus, a ring 45, which is now in the second position, i.e. at the bottom, indicates that a drilling or screwing into bone 400 through this hole in the hole section 3 has already taken place. This may be a significant advantage for the surgeon, since, for example, when using holes 3a, 3b, 3c in a quick sequence, it is always clear and unambiguous which of these holes have already been used. The rings 45 may be marked in several colors for better visibility, for example red for "already used" and green for "not yet used".

The ring 45 may be moved by the inserted receptacle 5, for example, by a projecting pin and shoulder on the insertion section 11 (see FIGS. 3a and 3b), which may engage in a lateral opening or groove on the holder or receptacle for the sleeve.

Figure 8:
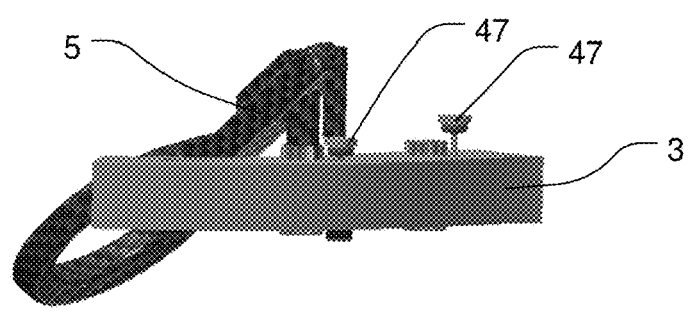
FIG. 8 shows the hole section with a display device in a further design.

FIG. 8 shows the hole section 3 with a further display device designed as pin 47. In this embodiment, the display shows whether e.g. a bore has already been drilled through this hole, not by a displaceable ring 45 as in the embodiment of FIG. 7, but by a pin 47 which is inserted into the hole section 3 and is thus in a second position. This insertion may be done manually or by the receptacle 5. The pin 47 may be marked in color for better visibility, for example red for "already used" and green for "not yet used".

FIG. 9a shows a cannulated screw 1 as first fastening device (or counterpart thereof) of the plate holder 200 with the plate 300.

FIG. 9b shows an instrument 15 inserted into the cannulated screw 1, in particular a drill. The cannulated screw 1 is funnel-shaped on the inside. This may be advantageous for drilling at a desired angle in order to fix the corresponding screw through plate 300 into bone 400 exactly in this position. Such a position may be necessary, for example, due to the bone anatomy.

FIG. 10 shows an alternative embodiment of a fixing of the plate holder 200 with the plate 300. The first fastening device of the plate holder 200 with the plate 300 in this embodiment is a wire connection. The wire connection comprises a wire 49 which is looped around the plate 300 and the plate holder 200 and thus fixes the plate holder 200 to the plate 300.

FIG. 11a shows another alternative method of fixing the plate holder 200 with the plate 300. The first fastening device of the plate holder 200 with the plate 300 in this embodiment is a clamp device with a clamp 51 and a pin 53. The pin 53 may be referred to as an interlocking pin or a securing pin. The clamp 51 is pushed onto the plate 300 (from the narrow to the wider cross-section) and fixed to the plate 300 using the pin 53. The holes may subsequently be drilled.

FIG. 11b shows the clamp 51 pushed onto the plate 300 from below, i.e. turned by 180 degrees compared to the view in FIG. 11a.

Figure 12A:
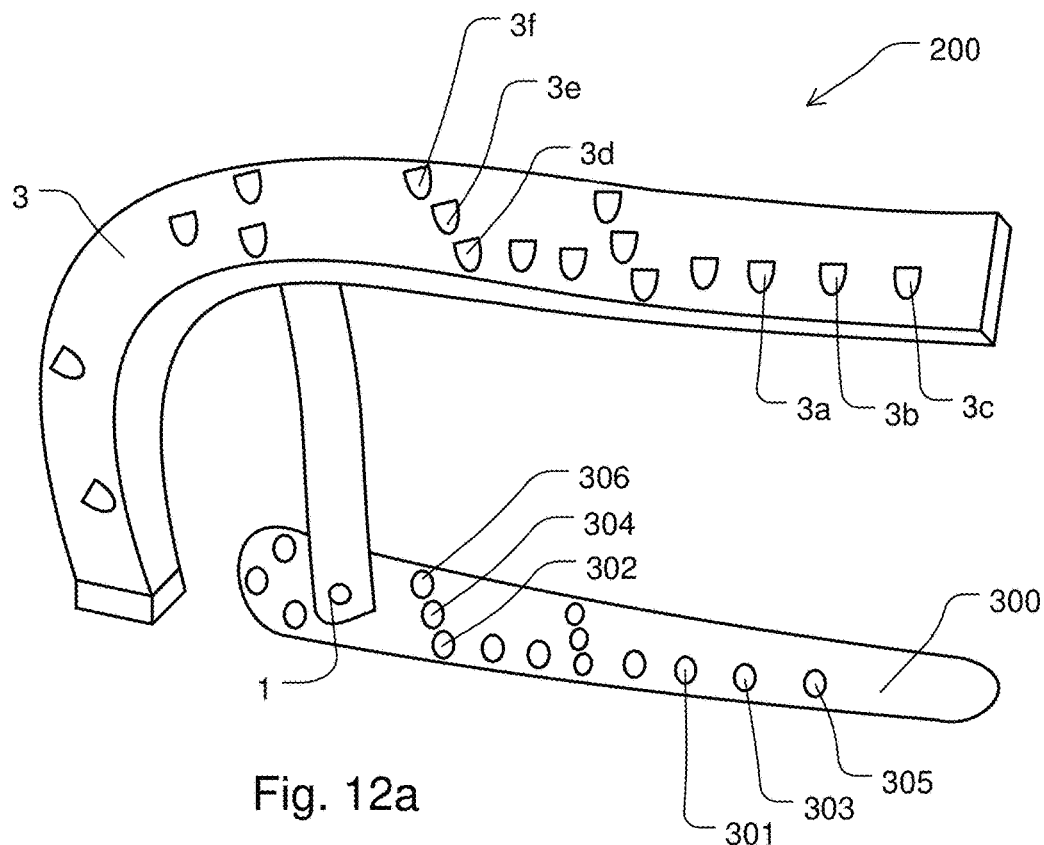
FIG. 12*a* shows, schematically simplified, a further plate holder with a further hole section.

FIG. 12a shows, schematically simplified, a further plate holder 200 according to the present invention with a further hole section 3 with holes 3a, 3b, 3c, 3d, 3e, 3f. For better clarity, the receptacle 5 and an optional support device 35 are not shown, as they are illustrated for example in FIG. 4a.

The plate holder 200 encompasses a first fastening device 1 for releasably fastening the plate holder 200 to the plate 300.

Unlike the embodiment shown in FIG. 4a, the hole section 3 in FIG. 12 not only comprises holes, for example 3a, 3b, 3c, in, or substantially in, the longitudinal direction of the hole section 3, but also holes 3d, 3e, 3f, which are offset transversely with respect to the longitudinal direction of the hole section 3. By these offset holes 3d, 3e, 3f, plates 300 may be fixed and screwed, which likewise comprise holes 302, 304, 306 of the plate 300 which are offset transversely with respect to the longitudinal direction of the plate 300.

Purely exemplarily, the offset holes 3*d*, 3*e*, 3*f* form a row of holes 3*d*, 3*e*, 3*f* arranged one behind the other. The angle of the straight line on which this row lies, in relation to the longitudinal alignment of the hole section 3, has in this embodiment purely exemplarily a value of approx. 60 degrees.

The holes 3*a*, 3*b*, 3*c*, 3*d*, 3*e*, 3*f*, or at least one hole, several arbitrary holes or all holes may be designed to be rotationally secure. A rotation-proof design does not permit rotation of, for example, an insert section, a pin or a third fastening device 11, as they are shown exemplarily in FIG. 3*a* and FIG. 3*b*, about its/their longitudinal axis. A rotation-proof design may, for example, have a hole cross-sectional shape with an asymmetrical, non-circular, oval, U-shaped, polygonal (e.g. inner triangular shape, inner square shape, inner hexagonal shape) and/or an inner hexagonal round shape. The element to be inserted may have a corresponding cross-sectional shape.

The holes 3*a*, 3*b*, 3*c*, 3*d*, 3*e*, 3*f*, at least one hole, any number of holes or all holes, are optionally not provided and designed for receiving a navigation device 9 or a tissue protection sleeve 37, as they are illustrated in FIG. 1 or FIG. 4*b*.

The longitudinal axes of the holes 3*a*, 3*b*, 3*c*, 3*d*, 3*e*, 3*f*, at least of any two holes 3*a*, 3*b*, 3*c*, 3*d*, 3*e*, 3*f*, may be arranged parallel or non-parallel to each other. For example, non-parallel axes of holes 3*a*, 3*b*, 3*c*, 3*d*, 3*e*, 3*f* may be assigned to corresponding non-parallel axes of holes 301, 302, 303, 304, 305, 306 of a plate 300 in order to be able to fix the plate 300 by screws. This assignment may be done, for example, by means of the holder 5 (see FIG. 1). Particular embodiments of plates 300 for tubular bones may have such non-parallel axes of holes 301, 302, 303, 304, 305, 306.

The holes 3*a*, 3*b*, 3*c*, 3*d*, 3*e*, 3*f*, at least any two holes 3*a*, 3*b*, 3*c*, 3*d*, 3*e*, 3*f*, may be arranged at different heights, for example at their upper stop surface or at the upper edge of the respective hole 3*a*, 3*b*, 3*c*, 3*d*, 3*e*, 3*f*. Such different heights are exemplarily shown in FIG. 1. These different heights may correspond to different heights of corresponding holes 301, 302, 303, 304, 305, 306 of a plate 300. For example, a receptacle 5 may be inserted and/or fixed in a hole 3*a*, 3*b*, 3*c*, 3*d*, 3*e*, 3*f* using a pin 11, so that a screw may be screwed directly into a suitable hole 301, 302, 303, 304, 305, 306 of plate 300 or into the bone. If the further holes 3*a*, 3*b*, 3*c*, 3*d*, 3*e*, 3*f* are already arranged and configured such that they also directly correspond to the respective holes 301, 302, 303, 304, 305, 306 of plate 300, a quick screwing of the plate 300 may be performed. This may advantageously enable a short operation duration.

Thus, a short operation duration may be advantageously enabled. A short operation duration may improve the patient's healing process and/or reduce the costs of the operation.

Figure 12B:
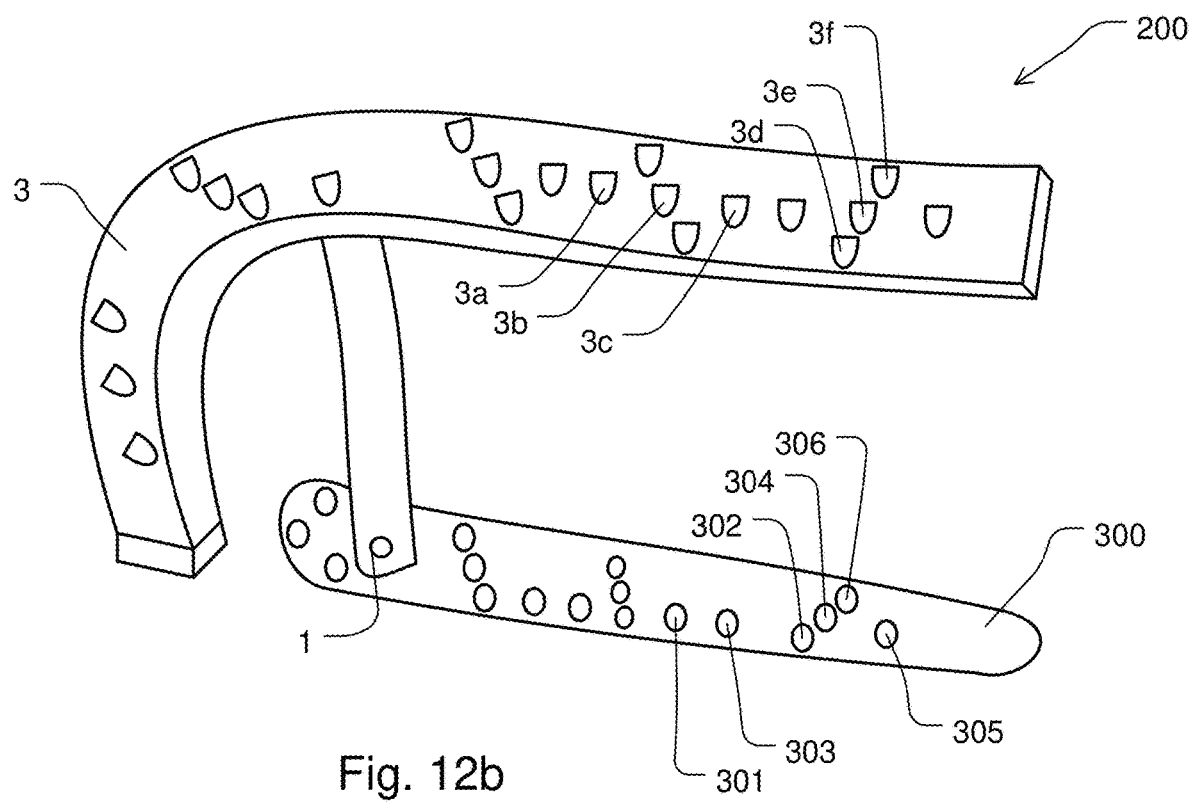
FIG. 12*b* shows a further arrangement of the holes in the hole section compared to the embodiment in FIG. 12*a*.

FIG. 12*b* shows a further arrangement of holes 3*a*, 3*b*, 3*c*, 3*d*, 3*e*, 3*f* in hole section 3 compared to the embodiment of FIG. 12*a*. Holes 3*d*, 3*e*, 3*f* are arranged at a different position in hole section 3 and at a different angle.

LIST OF REFERENCE NUMERALS 100 positioning device
200 plate holder or retainer
300 plate
301, 302, 303, 304 holes of the plate
305, 306, 308 holes of the plate
400 bone
1 cannulated screw; first fastening or fixing device
3 hole section; second fastening device
3*a*, 3*b*, 3*c* holes of the hole section
3*d*, 3*e*, 3*f* holes of the hole section
5 receptacle
7 adjustment device
9 navigation device
11 insertion section; pin; third fastening device
13 handle section
15 instrument
17 shoulder; display device
19 through-opening
21 recess
23 angle for navigation device
25 offset
27 spiral spring
29 sleeve
31 actuation or actuating pin
33 latching device
35 supporting device; receptacle
37 tissue protection sleeve
39 recess
41 plug-in pin; insertion section
45 rings; display device
47 pin; display device
49 wire; wire section
51 clamp
53 pin; interlocking pin

The invention claimed is:

1. A positioning device for positioning and/or fixing a plate to a bone, encompassing
   a plate holder, with a first fastening device for releasably fastening the plate holder to the plate, and with a second fastening device;
   an adjustment device; and
   a receptacle for the adjustment device, wherein the adjustment device comprises at least one navigation device, and wherein the navigation device is shaped to receive an interlocking device and/or an instrument that is positionable using the navigation device;
   wherein the receptacle comprises or is connected to a third fastening device;
   wherein an element of a group, which consists of the second fastening device and the third fastening device, includes a hole section with several holes, and wherein the other element of the group is designed as an insertion section, wherein the insertion section and the holes are designed for releasably connecting the second fastening device to the third fastening device.

2. The positioning device according to claim 1, wherein the plate holder comprises a handle section.

3. The positioning device according to claim 1, wherein each of the holes has a longitudinal axis, and wherein not all longitudinal axes of the holes are parallel to each other.

4. The positioning device according to claim 1, wherein the holes are arranged in one row, not in multiple rows.

5. The positioning device according to claim 1, wherein at least one of the holes of the hole section comprises a rotation-stop for preventing rotation of an inserted insertion section, wherein the rotation-stop has an asymmetrical, cross-sectional shape.

6. The positioning device according to claim 1, wherein the first fastening device of the plate holder comprises a cannulated screw or an element that connects to the cannulated screw.

7. The positioning device according to claim 6, wherein the cannulated screw is connected to a funnel-shaped extension or is arranged adjacent to the funnel-shaped extension.

8. The positioning device according to claim 1, wherein the hole section is non-releasably connected to the receptacle or to the plate holder.

9. The positioning device according to claim 1, wherein at least one of the holes of the hole section includes a display device which is shiftable from a first position into a second position to indicate that the third fastening device having the form of an insertion section has already been inserted into the relevant hole.

10. The positioning device according to claim 9, wherein the display device comprises a longitudinally displaceable ring which is displaceable from the first position into the second position.

11. The positioning device according to claim 9, wherein the display device has at least two different colors.

12. The positioning device according to claim 1, wherein the plate holder comprises a through-opening for the passage of a surgical.

13. The positioning device according to claim 1, further comprising a support device which is releasably connected to one of the several holes of the hole section.

14. The positioning device according to claim 13, wherein the support device is shaped to receive a rod therethrough.

15. The positioning device according to claim 1, wherein the plurality of holes are distinguishably marked from each other.

16. The positioning device according to claim 1, wherein the first fastening device comprises a section with a clamp and/or a pin.

17. The positioning device according to claim 1, wherein the first fastening device comprises a wire section.

18. The positioning device according to claim 1, which further comprises one or more locking devices or latching devices which are each associated with one of the holes and which releasably latch the insertion section in the respective hole.

19. The positioning device according to claim 1, connected to a plate for osteosynthesis, said plate having a plurality of through-openings for receiving one or more interlocking devices, wherein the depth of the through-openings each corresponds to a thickness of the plate, wherein holes of the plurality of holes are each associated with at least one or exactly one of the through-openings, wherein the adjustment device, when the insertion section is inserted into one of the holes, is designed such that the navigation device received in the adjustment device is aligned and movable, so that an interlocking device received in the navigation device or an instrument received in the navigation device, is movable with circumscription outside of or within a virtual cone surface, wherein a cone tip of the virtual cone surface comes to rest within the depth of the through-opening of the hole into which the insertion section is inserted.

20. The positioning device according to claim 1, wherein the plate holder comprises a handle section at an end side of the plate holder.

* * * * *